United States Patent [19]

Firnhaber et al.

[11] 3,979,470
[45] Sept. 7, 1976

[54] PROCESS FOR THE PRODUCTION OF PRIMARY NORMAL MONOCHLOROPARAFFINS

[75] Inventors: Bernhard E. Firnhaber, Somerville; Robert E. Chute, Clinton, both of N.J.; Brian H. Carter, Helsby, England

[73] Assignee: Pullman Incorporated, Chicago, Ill.

[22] Filed: Sept. 24, 1973

[21] Appl. No.: 400,459

[52] U.S. Cl............................ 260/658 R; 260/660
[51] Int. Cl.$^2$........................................ C07C 17/02
[58] Field of Search................ 260/658 R, 600, 660

[56] References Cited
UNITED STATES PATENTS

| | | | |
|---|---|---|---|
| 2,886,605 | 5/1959 | McClure et al................ | 260/658 R |
| 3,278,614 | 10/1966 | Michel et al.................... | 260/658 R |
| 3,426,086 | 2/1969 | Gray et al........................... | 260/660 |
| 3,505,418 | 4/1970 | Jubin................................. | 260/660 |

OTHER PUBLICATIONS
Groggins, Unit Processes in Organic Synthesis, McGraw-Hill Co. Inc., (1952), pp. 194–203.

Primary Examiner—James O. Thomas, Jr.
Assistant Examiner—James H. Reamer

[57] ABSTRACT

Primary normal monochloroparaffins are produced in high yields in a chlorination process of normal paraffins by the recycling technique of the present invention. By the recycling of secondary and nonprimary monochloroparaffin to the chlorination zone and the treatment of the polychlorinated compounds formed in the chlorination to form the primary normal monochloroparaffins and a recycle stream of paraffin and nonprimary monochloroparaffin, normal paraffins may be converted essentially completely to the desired primary normal monochloroparaffins. In a specific aspect of the present invention, alpha, omega-dichloroparaffins may be recovered if desired.

7 Claims, 2 Drawing Figures

PROCESS FOR THE PRODUCTION OF PRIMARY NORMAL MONOCHLOROPARAFFINS

BACKGROUND OF THE INVENTION

The present invention is directed to a process for the conversion of normal paraffins to produce primary normal monochloroparaffins. More particularly, the process is directed to the recycling of paraffins, secondary chloroparaffins, and nonprimary monochloroparaffins to the chlorination zone to obtain the desired primary chloroparaffins and polychlorinated compounds and then treating the polychlorinated compounds to dechlorinate these compounds with the formation of paraffin, nonprimary monochloroparaffins and the desired primary normal monochloroparaffins. The process is applicable to conversion of $C_3$ to $C_{15}$ paraffins to primary normal monochloroparaffins, but is particularly advantageous to the production of $C_3$ to $C_7$ primary normal monochloroparaffins; and if desired the valuable alpha, omega-chloroparaffins may be recovered. The yield of alpha, omega-dichloroparaffins may be increased by recycling primary monochloroparaffin to chlorination.

SUMMARY OF THE INVENTION

According to the present invention, high yields of the primary normal monochloroparaffins may be obtained in the chlorination of normal paraffins by the internal recycling technique of the present invention. The chlorination step is carried out to optimize the production of the primary chlorinated paraffin by chlorinating a feed of paraffin, secondary chloroparaffin and nonprimary chloroparaffins. The polychlorinated compounds produced in the chlorination step are subsequently treated in a dechlorination step which produces the corresponding paraffin, nonprimary chloroparaffins and desired primary normal monochloroparaffin. The desired primary normal monochloroparaffins are recovered and the remaining paraffin and chlorinated materials recycled. The dechlorination of the polychloroparaffins is preferably carried out in a single step of catalytic hydrogenolysis or the polychlorinated compounds may be treated in a two-step process including partial dehydrochlorination and selective hydrogenation. If desired, the alpha, omega-dichloroparaffins may be recovered from the process of the present invention or they may be produced as the main product by recycling primary monochloroparaffin to chlorination.

DESCRIPTION OF THE PREFERRED EMBODIMENT

Figure 1:
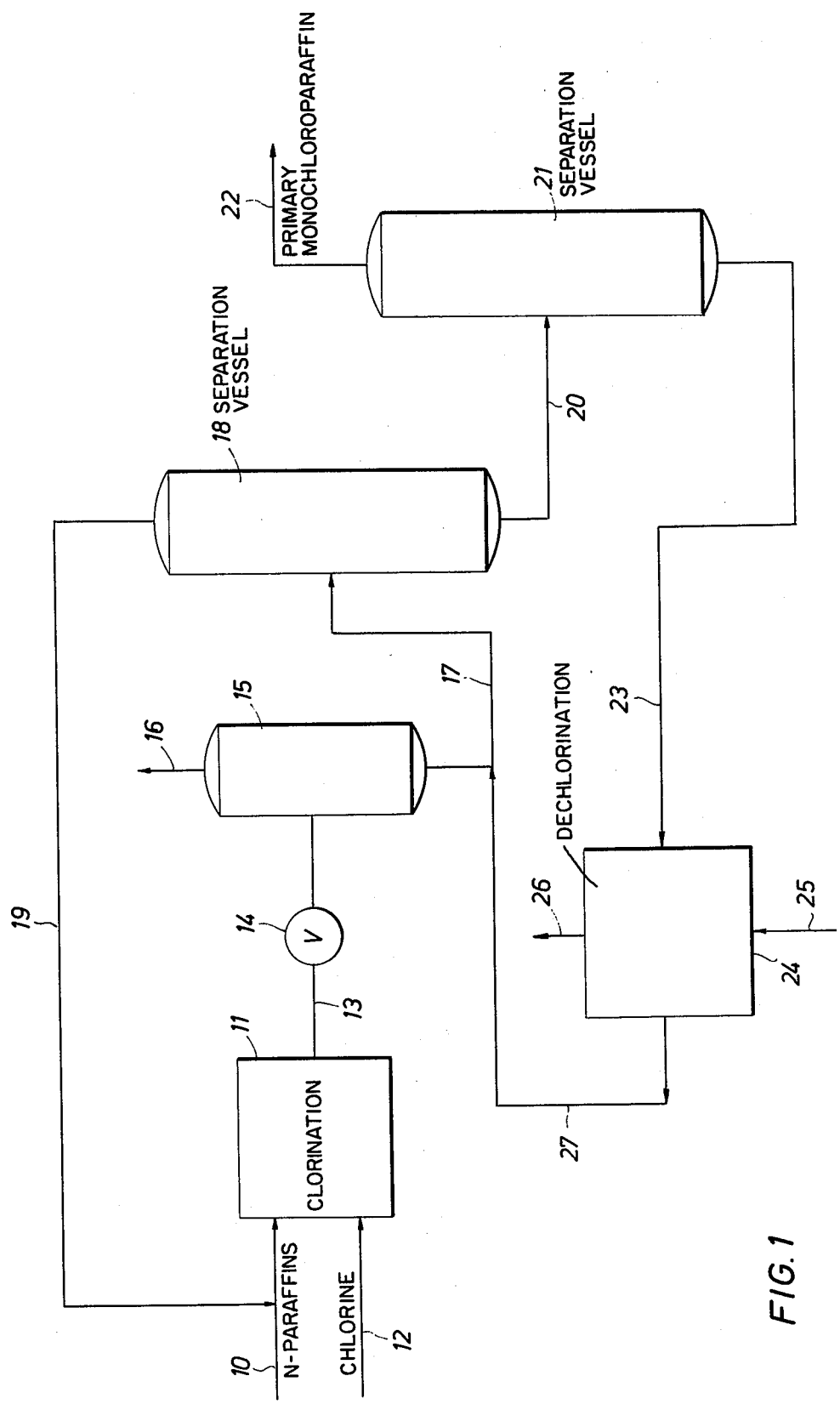
FIG. 1 is a schematic diagram of the process of the present invention.

Referring to FIG. 1 of the drawings, normal paraffin, preferably a $C_3$ to $C_7$ normal paraffin, is introduced by line 10 into a chlorination reactor 11. Chlorine is introduced by line 12 into the reactor 11. While the particular chlorination process in its specific aspect is not a material aspect of the present invention, a plug-flow chlorination reactor is preferred in that it optimizes the production of the primary monochloroparaffin. The plug-flow reaction may be carried out in liquid or in vapor phase and may be initiated thermally or by irradiation. Important to the present invention is that the chlorination reaction follow the course of a free-radical mechanism.

In the case of a thermal, liquid-phase chlorination, the chlorinated products are removed from reactor 11 by line 13 and passed through a pressure letdown valve 14 wherein the reaction products are introduced into flash vessel 15. The hydrogen chloride formed in the reaction is removed overhead by line 16. The reaction products are removed by line 17 from flash vessel 15 and passed to a separation vessel 18. The separation vessel 18 is the center of the internal (figure 8) recycling technique of the present invention since the normal paraffin and secondary chloroparaffins or nonprimary chloroparaffins are removed overhead by line 19 to be recycled and introduced into the feed line 10 for the chlorination reactor 11. On the other hand the desired primary chloroparaffins and di- and polychlorinated (hereafter simply polychlorinated) compounds are removed from the bottom of separation vessel 18 by line 20 and introduced into a separation vessel 21 wherein the desired primary chloroparaffins are recovered overhead by line 22 and separated from the polychlorinated compounds which are removed by line 23.

The polychlorinated compounds removed by line 23 from the bottom of separation vessel 21 are introduced to a dechlorination step 24. The dechlorination step 24 utilizes hydrogen which is introduced by line 25 with the production of hydrogen chloride which may be removed by line 26. It has been found that in the dechlorination step 24 the primary monochloroparaffin may be produced since the primary chlorine attached to the paraffin moiety is the more difficult chlorine to remove and thus the primary monochloroparaffin and the alpha, omega dichloroparaffin is preferentially produced in this step. The products from the dechlorination step 24 are recycled to line 17 for further separation and treatment.

According to the present invention, the chlorination reaction is preferably a thermal liquid phase chlorination carried out in a plug-flow reactor. The exothermic chlorination reaction is therefore initiated at temperatures of 250° F. —500° F. and pressures from about 25 to about 75 atmospheres. The conversion level is maintained at 10 to 50% and preferably 15 to 25% conversion per pass. By recycling the secondary chloroparaffins, the chlorination results in a higher percentage substitution in the primary position than that of the normal paraffin, e.g. as shown in Table 1.

TABLE 1

| Carbon No. | % Substitution in Primary Position | |
|---|---|---|
| | n-Paraffin | Secondary Chloroparaffin |
| 4 | 38.4 | 46.2 |
| 6 | 23.8 | 31.3 |
| 8 | 17.2 | 21.1 |

Hence, the recycling of a stream to the chlorination step is to obtain greater primary substitution over the selectivities obtained in the chlorination of the paraffin alone. If single carbon number normal paraffins are processed, the primary and secondary monochloroparaffins can be separated by distillation, e.g. separation vessel 18. While distillation is preferred, separation may also be accomplished by solvent extraction.

Figure 2:
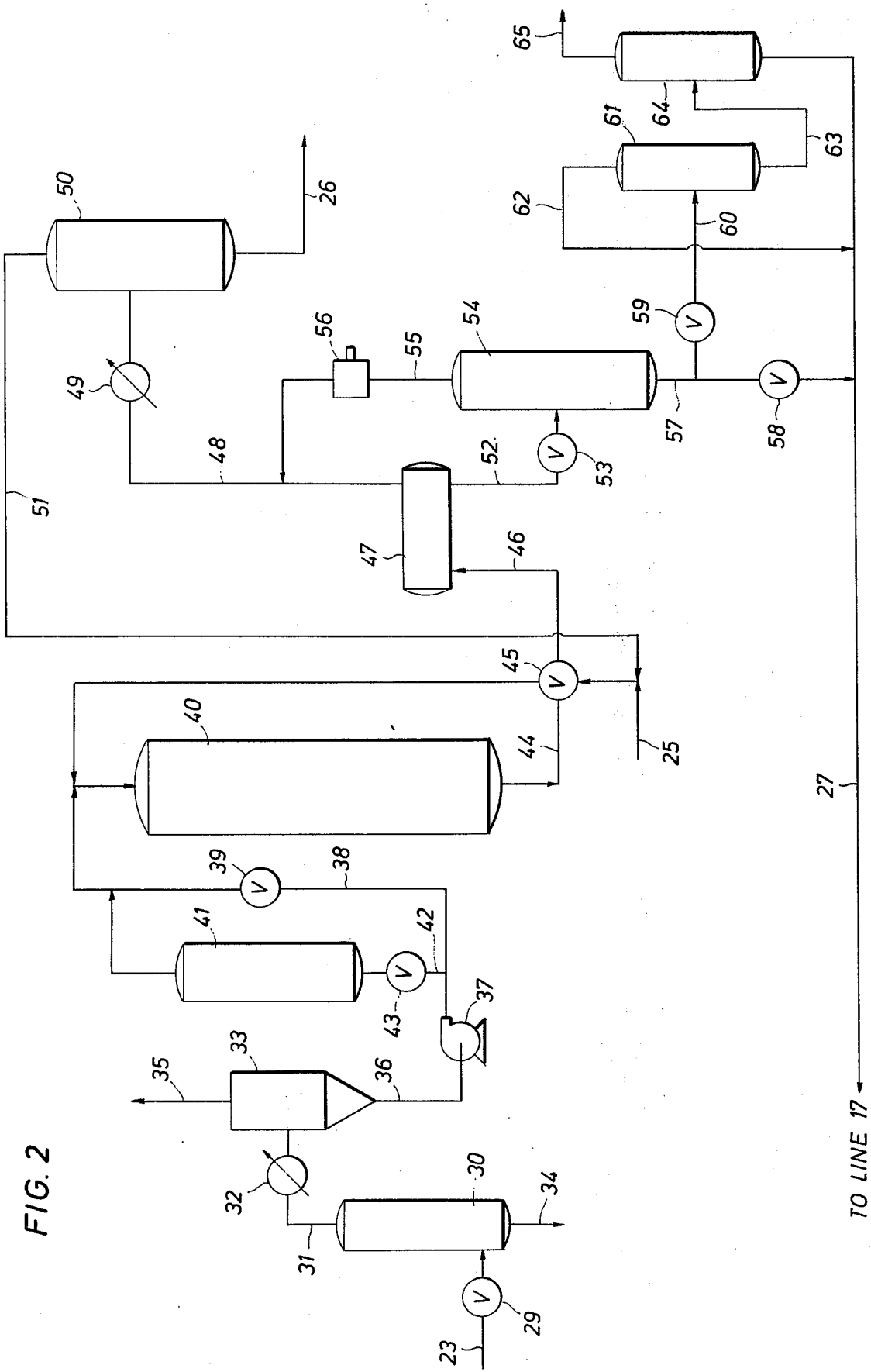
FIG. 2 is a schematic diagram of the catalytic hydrogenolysis step.

Large amounts of the polychlorinated (di, tri, etc., substituted) compounds are converted in the dechlorination step 24 to the corresponding paraffin, primary monochloroparaffin and secondary monochloroparaffin which are then recycled to line 17 for separation and treatment. The dechlorination step 24 is preferably a single step process of catalytic hydrogenolysis although the polychlorinated compounds may be treated in two steps by partial dehydrochlorination followed by selective hydrogenation. Referring to FIG. 2, the polychlorinated compounds are removed from the bottom of separation vessel 21 by line 23 and passed through valve 29 before being introduced into a vacuum vessel 30. At least 95% of the polychlorinated products are removed overhead from vessel 30 by line 31 where the vapors are passed through condenser 32 before entering a vacuum flash vessel 33. The residual bottoms are removed from vessel 30 by line 34. The vacuum which is drawn from line 35 results in a vacuum flash separation within vacuum vessel 30. Any metallic or heavy polychlorinated compounds are removed through the heavy bottoms line 34 to prevent any coking or rapid catalyst deactivation in the dechlorination step 24 of the process of the present invention. The vacuum flash step, while showing only one vessel may utilize two or more vessels with the heavy materials and metallic impurities thus removed from the system. The condensed polychlorinated compounds are passed through line 36 to pump 37 which feeds the liquid at a pressure of about 50 to about 100 atmospheres through line 38 and valve 39 to a hydrogenolysis reactor 40. In line 38 may be a guard chamber 41 which is connected to line 38 by line 42 having a valve 43 therein which together with valve 39 controls the amount of material passing through the guard chamber 41. The guard chamber 41 is packed with an absorbent as, for example, alumina or silica gel to remove any metallic impurities from the liquid charge of polychlorinated compounds to the hydrogenolysis reactor 40.

The hydrogenolysis reactor 40 is packed with a noble metal catalyst, preferably platinum or palladium on a support. The support material is selected from those having low inherent acidity to prevent isomerization and/or cracking. The support is preferably a silica of 99+% purity. Other high surface materials of low acidity may also be used as supports. A pure alumina may also be used; however, a mixed alumina-silica support is more acidic, thus, it was found that a mixed support containing 4% alumina had considerable isomerization and cracking activity. The noble metal is present in concentrations of about 0.2 to 2% or greater by weight and preferably concentrations of between 0.5 and 1% by weight. Conditions in the hydrogenolysis reactor 40 are maintained at pressures between 10 and 100 atmospheres preferably between 50 and 100 atmospheres for efficient recovery of HCl, and at temperatures between 250° F. and 450° F. Hydrogen is introduced by line 25 to the reactor 40. It has been found under the conditions of temperature and pressure that both dehydrochlorination and hydrogenation occur on the catalyst in the single reactor with the polychloroparaffins being converted to paraffins, primary monochloroparaffins, secondary monochloroparaffins and hydrogen chloride.

The liquid product produced in the hydrogenolysis reactor 40 is removed by line 44, passes through a heat exchanger 45 and by line 46 to a gas liquid separator 47. Most of the gas is hydrogen or hydrogen chloride. The gas is removed by line 48, cooled in a heat exchanger 49 and passed to a separation vessel 50. The hydrogen, containing some hydrogen chloride is removed overhead from the separation vessel 50 by line 51 where it may be recycled and mixed with the fresh hydrogen feed, introduced by line 25, for introduction into the hydrogenolysis reactor 40. The fresh hydrogen feed and recycle feed is passed through the heat exchanger 45 before introduction into the hydrogenolysis reactor 40. Liquid hydrogen chloride is removed from separation vessel 50 by line 26. The liquid portion separated in gas liquid separator 47 is removed by line 52 and passed through a letdown valve 53 before being introduced into a separation vessel 54. Any remaining gases such as hydrogen or hydrogen chloride are removed overhead from vessel 54 by line 55 and passed through a compressor 56 before being combined with the gases in line 48 and the heat exchanger 49 prior to introduction into separation vessel 50. The remaining liquid portion from separation vessel 54 may then be removed by line 5 and passed through valve 58 into line 27 for recycling into line 17 for introduction into the separation vessel 18.

The dechlorination step 24 and especially hydrogenolysis converts the polychlorinated paraffins with the removal of chlorine in the secondary position selectively over chlorine in the primary position. At polychloroparaffin conversions of 90% and lower per pass, the conversion of primary chloride is negligible. However, the selectivity to secondary monochloroparaffin decreases rapidly with polychloroparaffin conversion. Because of the previously described beneficial effect of recycling secondary monochloroparaffin to chlorination for production of primary chloroparaffins, the preferred conversion in hydrogenolysis is 30 – 70% per pass.

Polychloroparaffins with two or more chlorine atoms in the primary position will build up in the dechlorination or hydrogenolysis recycle loop. Of these compounds alpha, omega-dichloroparaffin is formed in by far the largest amounts. The alpha, omega-dichloroparaffin may be recovered from the hydrogenolysis product stream by distillation. After sufficient build-up, product may be taken from line 57 through valve 59 in line 60 and passed to a first separation vessel 61. A light overhead cut is removed by line 62 which is recycled through line 27. The heavy cut, containing the desired dichloroparaffin or other products, is passed by line 63 to a second separation vessel 64 wherein the desired product is recovered by line 65. The yield of alpha, omega-dichloroparaffin may be increased above the naturally occurring yield by recycling part or all of the primary monochloroparaffin to chlorination. This will best be done by recovering the necessary amount of primary chloroparaffin overhead from separation vessel 18 along with paraffin and secondary chloroparaffin for recycle to chlorination.

It can be seen that by the internal recycling (figure 8) configuration that the chlorination step optimizes the chlorination of the paraffin feed for placing a chlorine atom at the primary position of the paraffin moiety while on the other hand, the dechlorination of the polychlorinated compounds removes the chlorine atoms selectively from all positions except the primary position of the paraffin moiety. The resulting products therefore are the desired primary monochloroparaffins and/or the alpha, omega-dichloroparaffins.

Furthermore, the concept of this invention allows a wide variation of product composition. Recovery of part of the secondary monochloroparaffin will lead to coproduction of primary and secondary monochloroparaffin in the desired ratio. A combination of partial recovery of secondary monochloroparaffin and partial recycle of primary monochloroparaffin will produce primary and secondary chloroparaffin and alpha, omega-dichloroparaffin in the desired ratio.

The present invention will be further illustrated by the following specific examples, which are given by way of illustration and not as limitations on the scope of the present invention.

EXAMPLE 1

The following four tests were carried out to demonstrate the effect of recycling of primary and secondary monochloroparaffin on the respective yields of primary and secondary monochloroparaffin and alpha, omega-dichloroparaffin.

Normal butane was chlorinated, without and with addition of 2-chlorobutane and 1-chlorobutane to the butane feed, in the vapor phase in a tubular reactor, at a maximum reactor temperature of 390° C. and a residence time of 0.2 seconds. Preheated hydrocarbon and chlorine feed were effectively mixed in a double-jet mixer immediately before entering the reactor. Chlorine conversion was complete. Carbon formation during chlorination was in all tests less than 0.01% of the butane feed. Feed ratios and product distributions on an HCl-free basis were as set forth in Table 2.

The polychlorobutane was recovered from the liquid chlorination products by distilling lower boiling n-butane and monochlorobutane overhead, separately for the individual tests. The four polychlorobutane samples were then subjected to a catalytic hydrogenolysis by passing the vaporized polychlorobutane mixed with hydrogen at a mole ratio of 1:6 over a catalyst composed of 0.7% Pd on pure silica at 180° C. under a pressure of 215 psia and at a space velocity of 3 volumes liquid feed per volume catalyst per hour. Maintaining a conversion of approximately 45% per pass and recycling unconverted polychlorobutane until the recycle consisted of approximately 90% 1,4-dichlorobutane, following selectivities were obtained in polychlorobutane hydrogenolysis as set forth in Table 3.

By subtracting the recycled amounts of n-butane, 2-chlorobutane, 1-chlorobutane, the ultimate selectivities were calculated for the four tests as set forth in Table 4.

TABLE 2

| Test No. | Feed Mole Ratios | | | Product Distribution, Mol % | | | |
|---|---|---|---|---|---|---|---|
| | n-Butane Chlorine | 2-Chlorobutane Chlorine | 1-Chlorobutane Chlorine | n-Butane | 2-Chloro-butane | 1-Chloro-butane | Polychloro-butane |
| 1 | 5 | 0 | 0 | 80.9 | 11.4 | 6.8 | 0.9 |
| 2 | 2 | 2 | 0 | 33.6 | 52.6 | 5.5 | 8.3 |
| 3 | 2 | 1 | 1 | 34.7 | 30.7 | 25.3 | 9.3 |
| 4 | 2 | 0 | 2 | 35.7 | 8.3 | 45.8 | 10.2 |

TABLE 3

| Test No. | Mol % Selectivity in Hydrogenolysis of Polychlorobutane to: | | | |
|---|---|---|---|---|
| | n-Butane | 2-Chlorobutane | 1-Chlorobutane | 1,4-Dichlorobutane |
| 1 | 12.5 | 12.5 | 59.2 | 15.8 |
| 2 | 21.7 | 21.8 | 52.7 | 3.8 |
| 3 | 10.1 | 10.0 | 60.8 | 19.1 |
| 4 | 1.7 | 1.7 | 66.6 | 30.0 |

TABLE 4

| Test No. | n-Butane Conversion % Per Pass | Ultimate Selectivity, % of Converted n-Butane | | |
|---|---|---|---|---|
| | | 2-Chlorobutane | 1-Chlorobutane | 1,4-Dichlorobutane |
| 1 | 19.0 | 60.5 | 38.7 | 0.8 |
| 2 | 29.2 | 30.0 | 67.8 | 2.2 |
| 3 | 28.8 | 46.3 | 41.3 | 12.4 |
| 4 | 28.3 | 60.7 | 17.6 | 21.7 |

EXAMPLE 2

This experiment was carried out in a continuous, integrated unit to demonstrate the conversion of n-heptane to 100% 1-chloroheptane.

Fresh n-heptane feed (1.00 mol/hr) combined with a recycle from fractionation tower I of 8.45 mol/hr n-heptane and 17.66 mol/hr secondary chloroheptane was charged, at ambient temperature and 80 psia pressure to the top of a packed absorption vessel into which 4.55 mol/hr chlorine, completely vaporized and at a temperature of 38° C. was introduced at the bottom and was completely absorbed in the liquid. The chlorine-heptane-chloroheptane solution from the chlorine absorber was pumped at a pressure of 700 psia through a heat exchanger to the tubular chlorination reactor. The solution entered the adiabatic reactor at 300° F., a temperature sufficient to initiate the chlorination reaction, and left after 10 seconds residence time and complete chlorine conversion.

The chlorination product after cooling, decompression and stripping of HCl, consisting of 27.9 mole % unconverted n-heptane, 61.8 mol % secondary chloroheptane, 1.3 mole % 1-chloroheptane, and 9.0 mole % polychloroheptane, was combined with the produce of hydrogenolysis before entering fractionation tower I where the combined stream was separated in an overhead stream of n-heptane and secondary chloroheptane for recycle to chlorination and a bottom stream of 1-chloroheptane and polychloroheptane. This bottom stream was separated in fractionation tower II in 1.00 mol/hr 1-chloroheptane produce as overhead and 4.06 mole/hr polychloroheptane as bottom product.

The polychloroheptane was pumped to 100 psia pressure, passed through a guard absorber bed, heated to 175° C., and mixed with 20 mol/hr dry hydrogen of the same temperature and pressure at the top of the hydrogenolysis reactor. The combined feed flowed co-currently downward through a packed bed of 0.7% palladium on silica beads at a space velocity of 3 volumes liquid polychloroheptane feed per volume catalyst per hour. Reactor effluent at 205° C consisted of 16.45 mol/hr hydrogen, 3.55 mol/hr HCl, 0.89 mol/hr n-heptane, 0.89 mol/hr secondary chloroheptane, 0.65 mol/hr 1-chloroheptane, and 1.63 mol/hr polychloroheptane. The hydrogenolysis product after condensing and separation from hydrogen and hydrogen chloride was combined with the chlorination product for further processing.

The nature and objects of the present invention having been completely described and illustrated and the best mode thereof contemplated set forth, what we wish to claim as new and useful and secure by Letters Patent is:

1. A process for the production of primary normal monochloroparaffins from a $C_3$ to $C_{15}$ normal paraffin which comprises:
   chlorinating said normal paraffin and the corresponding secondary chloroparaffin using a free-radical mechanism and conditions to optimize the substitution in the primary position of said paraffins to form a product containing unreacted normal paraffin, primary monochloroparaffin, secondary chloroparaffin and polychlorinated compounds;
   separating said product whereby said normal paraffin and corresponding secondary chloroparaffin are separated from the primary monochloroparaffin and polychlorinated compounds;
   recycling said normal paraffin and corresponding secondary chloroparaffin to said chlorination step;
   separating said polychlorinated compounds from said primary monochloroparaffin and recovering said primary monochloroparaffin;
   dechlorinating said polychlorinated compounds with hydrogen in the presence of a noble metal at temperatures of 250° to 500°F. and pressures of 25 to 75 atmospheres to convert said polychlorinated compounds to paraffin, primary monochloroparaffin, secondary monochlorparaffin and hydrogen chloride;
   separating said hydrogen chloride from said mixture of paraffin, primary normal monochloroparaffin and secondary monochlorparaffin; and
   combining said mixture with said product formed in said chlorinating step prior to separation of said product whereby the primary normal monochloroparaffin may be recovered.

2. A process according to claim 1 wherein said chlorination step is carried out in a plug-flow chlorination reactor.

3. A process according to claim 1 wherein said chlorination step is a thermal, liquid phase chlorination.

4. A process according to claim 1 whereby alpha, omega-dichloroparaffin builds up in said dechlorination recycle loop and recovering said alpha, omega-dichloroparaffin.

5. A process according to claim 3 wherein the conversion level is maintained at 10 to 50% per pass in said chlorination step.

6. A process according to claim 3 wherein the conversion level is maintained at 30 to 70% per pass in said hydrogenolysis step.

7. A process according to claim 4 wherein part of the primary monochloroparaffin is recycled with normal paraffin and secondary chloroparaffins to the chlorination step in order to increase the yield of said alpha, omega-dichloroparaffin.

* * * * *